US006712955B1

(12) United States Patent
Hou et al.

(10) Patent No.: US 6,712,955 B1
(45) Date of Patent: *Mar. 30, 2004

(54) SLURRY HYDROPROCESSING USING BULK MULTIMETALLIC CATALYSTS

(75) Inventors: Zhiguo Hou, Baton Rouge, LA (US); Roby Bearden, Jr., Baton Rouge, LA (US); Ferrughelli Thomas David, Flemington, NJ (US); Sabato Miseo, Pittstown, NJ (US); Martin Leo Gorbaty, Westfield, NJ (US); Stuart Leon Soled, Pittstown, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/869,983

(22) PCT Filed: Jan. 14, 2000

(86) PCT No.: PCT/US00/00994

§ 371 (c)(1), (2), (4) Date: Aug. 22, 2001

(87) PCT Pub. No.: WO00/42127

PCT Pub. Date: Jul. 20, 2000

Related U.S. Application Data

(63) Continuation-in-part of application No. 09/231,156, filed on Jan. 15, 1999, now Pat. No. 6,162,350, which is a continuation-in-part of application No. 08/900,389, filed on Jul. 15, 1997, now Pat. No. 6,156,695.

(51) Int. Cl.[7] .............................................. C10G 45/60
(52) U.S. Cl. ................... 208/216 R; 208/108; 208/215; 208/254 H; 208/217
(58) Field of Search ............................ 208/216 R, 108, 208/215, 254 H, 217

(56) References Cited

U.S. PATENT DOCUMENTS

| 4,596,785 A | 6/1986 | Toulhoat et al. ............ 502/220 |
| 4,721,558 A | 1/1988 | Jacobson et al. ........... 208/108 |
| 6,162,350 A | * 12/2000 | Soled et al. ................ 208/113 |

FOREIGN PATENT DOCUMENTS

| EP | 0419266 A1 | 9/1989 | ........... C10G/45/16 |
| WO | WO99/03578 | 1/1999 | ........... B01J/23/883 |

* cited by examiner

*Primary Examiner*—Walter D. Griffin
*Assistant Examiner*—James Arnold, Jr.
(74) *Attorney, Agent, or Firm*—G. J. Hughes

(57) ABSTRACT

A slurry hydroprocessing process for upgrading a hydrocarbon feedstock containing nitrogen and sulfur using bulk multimetallic catalyst comprised of at least one Group VIII non-noble metal and at least two Group VIB metals wherein the ratio of Group VIB metal to Group VIII metal is about 10:1 to about 1:10.

8 Claims, 2 Drawing Sheets

SLURRY HYDROPROCESSING USING BULK MULTIMETALLIC CATALYSTS

CROSS REFERENCE TO RELATED APPLICATIONS

This is a continuation-in-part of U.S. Ser. No. 09/231,156 now U.S. Pat. No. 6,162,350 filed on Jan. 15, 1999, which is a continuation-in-part of U.S. Ser. No. 08/900,389 now U.S. Pat. No. 6,156,695 which was filed on Jul. 15, 1997.

FIELD OF THE INVENTION

This invention relates to a slurry hydroprocessing process for upgrading a hydrocarbon feedstock containing nitrogen and sulfur using bulk multimetallic catalyst comprised of at least one Group VIII non-noble metal and at least two Group VIB metals wherein the ratio of Group VIB metal to Group VIII metal is about 10:1 to about 1:10.

BACKGROUND OF THE INVENTION

Hydroprocessing includes a variety of processes wherein the quality of feedstocks, typically petroleum feedstocks, is improved by treating the same with hydrogen in the presence of a hydrotreating catalyst. Various types of reactions may occur during hydrotreating. In one type of reaction, mercaptans, such as disulfides, thiophenes, benzothiophenes and dibenzothiophenes are desulfurized. The thiophenes, mercaptans and disulfides are representative of a high percentage of the total sulfur in lighter feedstocks. Benzothiophenes and dibenzothiophenes appear as the predominant sulfur forms in heavier feeds such as light catalytic cracker cycle oil (LCCO) and vacuum gas oils (VGO). Hydroprocessing also removes nitrogen from various nitrogen compounds such as carbazoles, pyridines, and acridines. Hydrotreating can also hydrogenate aromatic compounds, existing as condensed aromatic ring structures with 1 to 3 or more aromatic rings such as benzene, alkyl substituted benzene, naphthalene, and phenanthrene.

The most common hydroprocessing process utilizes a fixed bed hydrotreater. A fixed bed system, however, has several disadvantages or inherent limitations. At relatively low temperatures and employing a conventional catalyst, a fixed bed system is characterized by relatively low reaction rates for the hydrogenation of multi-ring aromatics and the removal of nitrogen and sulfur in the material being treated. On the other hand, at relatively higher temperatures, a fixed bed system suffers from equilibrium limits with respect to the degree of aromatics hydrogenation.

Another limitation of a fixed bed system is the difficulty in controlling the temperature profile in the catalyst bed. As a result, exothermic reactions may lead to undesirably higher temperatures in downstream beds and consequently an unfavorable equilibrium. Still a further limitation of a fixed bed system is that a high pressure drop may be encountered, when employing small particle catalysts to reduce diffusion limits. Finally, a fixed bed system suffers from catalyst deactivation, which requires periodic shut-down of the reactor.

Hydroprocessing processes utilizing a slurry of dispersed catalysts in admixture with a hydrocarbon oil are generally known. For example, U.S. Pat. No. 4,952,306 teaches a slurry process for hydrotreating mid-distillates using a catalyst comprising catalyst particles 1 micron to ⅛ inch in average diameter and characterized by a predefined catalyst index as set forth in the claims.

Also, U.S. Pat. No. 4,557,821 to Lopez et al discloses hydrotreating a heavy oil employing a circulating slurry catalyst. Other patents disclosing slurry hydrotreating include U.S. Pat. Nos. 3,297,563; 2,912,375; and 2,700,015, all of which are incorporated herein by reference.

While conventional slurry hydroprocessing has met with varying degrees of commercial success, there still remains a need in the art for processes and slurry catalysts that result in improved yields and selectivity.

As the supply of low sulfur, low nitrogen crudes decrease, refineries are processing crudes with greater sulfur and nitrogen contents at the same time that environmental regulations are mandating lower levels of these heteroatoms in products.

In one approach, a family of compounds, related to hydrotalcites, e.g., ammonium nickel molybdates, has been prepared. Whereas X-ray diffraction analysis has shown that hydrotalcites are composed of layered phases with positively charged sheets and exchangeable anions located in the galleries between the sheets, the related ammonium nickel molybdate phase has molybdate anions in interlayer galleries bonded to nickel oxyhydroxide sheets. See, for example, Levin, D., Soled, S. L., and Ying, J. Y., Crystal Structure of an Ammonium Nickel Molybdate prepared by Chemical Precipitation, Inorganic Chemistry, Vol. 35, No. 14, p. 4191–4197 (1996). The preparation of such materials also has been reported by Teichner and Astier, Appl. Catal. 72, 321–29 (1991); Ann. Chim. Fr. 12, 337–43 (1987), and C. R. Acad. Sci. 304 (II), #11, 563–6 (1987) and Mazzocchia, Solid State Ionics, 63–65 (1993) 731–35.

Consequently, a need exists for increasingly efficient desulfurization and denitrogenation catalysts.

SUMMARY OF THE INVENTION

In accordance with the present invention there is provided a slurry hydroprocessing process which comprises hydroprocessing a hydrocarbon feedstock containing nitrogen and sulfur, at slurry hydrotreating conditions, in the presence of a hydrogen containing treat gas and in the presence of a bulk multimetallic catalyst comprised of at least one Group VIII non-noble metal and at least two Group VIB metals and wherein the ratio of Group VIB metal to Group VIII non-noble metal is from about 10:1 to about 1:10.

In a preferred embodiment the bulk multimetallic catalyst is a BMCatalyst bulk catalyst, said catalyst being represented by the formula: $(X)_b(Mo)_c(W)_dO_z$; wherein X is a non-noble Group VIII metal, and the molar ratio of b(c+d) is 0.5/1 to 3/1; the molar ratio of c:d is $\geq 0.01/1$; and z=[2b+6(c+d)]2, thereby resulting in a feedstock with reduced levels of both nitrogen and sulfur.

In another preferred embodiment of the present invention the Group VIII non-noble metal is selected from Ni and Co.

In still another preferred embodiment of the present invention the Group VIII metal is Ni, and the X-ray diffraction pattern of the catalyst is essentially amorphous with crystalline peaks at d=2.53 Angstroms and d=1.70 Angstroms.

In yet another preferred embodiment of the present invention the molar ratio of b: (c+d) is 0.75/1 to 1.5/1 and the molar ratio of c:d is 1/10 to 10/1.

In still another preferred embodiment of the present invention the distillate feedstock is a product of petroleum, synfuel, coal, shale oil, bitumen, or a tar sand conversion process.

In another preferred embodiment of the present invention the distillate boiling range feedstock boils in the range of about 175° to about 400° C.

In a preferred embodiment of the present invention the Group VIII non-noble metal is nickel.

In another preferred embodiment of the present invention the feedstock is hydroprocessed in the presence of the bulk multimetallic catalyst prepared by steps that comprise:

(a) adding to a hydrocarbon feedstock having a Conradson carbon content up to about 50 weight percent, one or more thermally decomposable metal compound in an amount sufficient to provide the ratio of atoms of feedstock Conradson carbon, calculated as elemental carbon, to atoms of metal constituents of said one or more thermally decomposable metal compounds of less than about 750 to 1, said metal constituent being at least one Group VIII non-noble metal and at least two Group VIB metals;

(b) heating said thermally decomposable metal compound within said feedstcok at an elevated temperature in the presence of a hydrogen-containing gas to produce a solid high surface area catalyst comprised of at least one Group VIII non-noble metal and at least two Group VIB metals wherein the ratio of Group VIB metal to Group VIII non-noble metal is about 10:1 to about 1:10; and (c) recovering said high surface area catalyst.

DETAILED DESCRIPTION OF THE INVENTION

Figure 1:
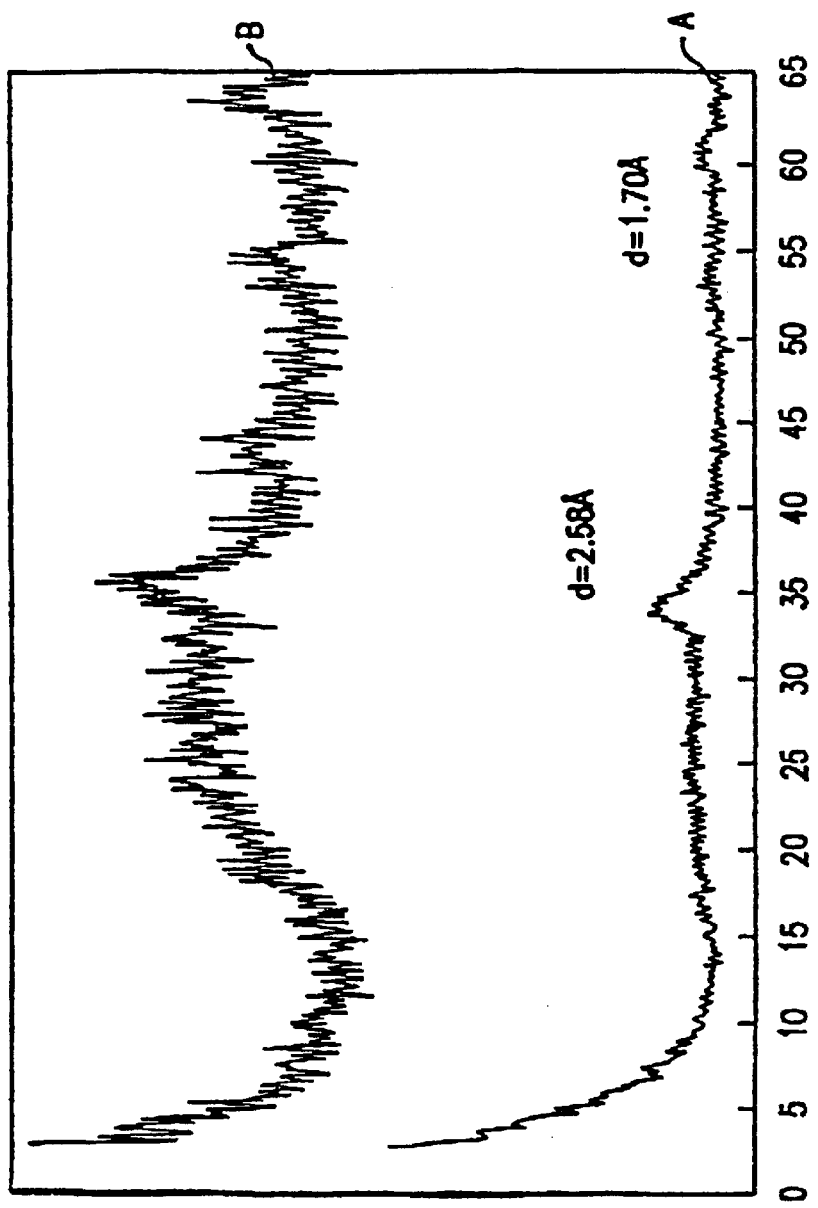
FIG. 1 is the X-ray diffraction pattern of a Ni—$Mo_{0.5}W_{0.5}$—O compound prepared by boiling precipitation before calcining (Curve A) and after calcining at 400° C. (Curve B). Note that the patterns for both the precursor and the decomposition product of the precursor are quite similar with the two peaks at essentially the same place. The ordinate is relative intensity; the abscissa is two theta (degrees).
Figure 2:
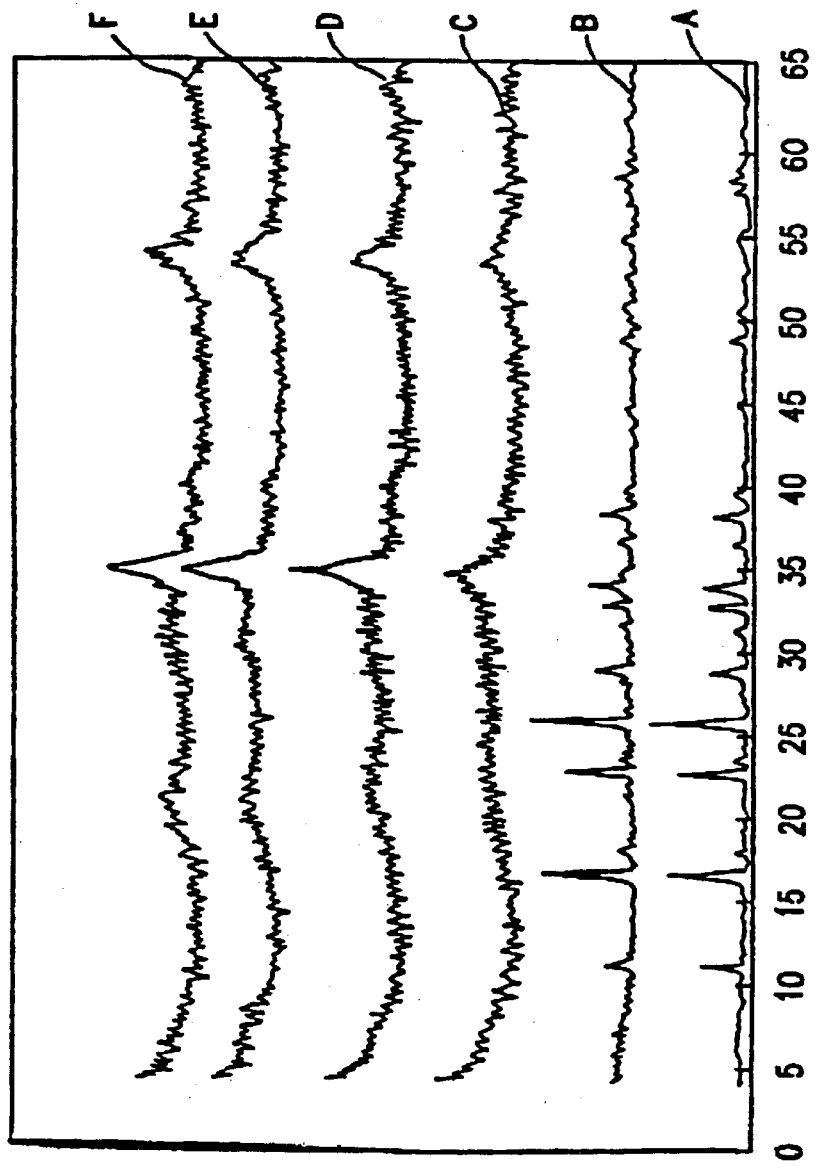
FIG. 2 shows the X-ray diffraction patterns, by CuKα radiation ($\lambda$=1.5405Å), of $NH_4$—Ni-$Mo_{1-x}$—Wx—O precursors wherein curve A is $Mo_{0.9}W_{0.1}$, curve B is $Mo_{0.7}W_{0.3}$, curve C is $Mo_{0.5}W_{0.5}$, curve D is $Mo_{0.3}W_{0.7}$, curve E is $Mo_{0.1}W_{0.9}$, and curve F is $Mo_0W_1$. The ordinate and abscissa are as described for FIG. 1.

The invention is based in part on the discovery that molybdenum in a Ni-Mo phase may be partially substituted by tungsten. The resulting phase is an essentially ammonia-free, substantially amorphous, oxide phase which upon sulfidation provides enhanced catalytic activity relative to the unsubstituted Ni-Mo phase. The invention is also based in part on the discovery of catalysts containing at least one Group VIII non-noble metal and at least two Group VIB metals, wherein the ratio of Group VIB metal to Group VIII non-noble metal is from about 10:1 to about 1:10.

The catalyst composition according to the invention can be used in virtually all hydroprocessing processes to treat a plurality of feeds under wide-ranging reaction conditions such as temperatures of from 200 to 450° C., metal component in a protic liquid in which the metal is at least partly present as a solid, and optionally partly dissolved in the protic liquid.

To obtain a bulk catalyst composition with high catalytic activity, it is therefore preferred that the metal components, which are at least partly in the solid state during contacting, are porous metal components. It is desired that the total pore volume and pore size distribution of these metal components is approximately the same as those of conventional hydrotreating catalysts. Conventional hydrotreating catalysts generally have a pore volume of 0.05–5 ml/g, preferably of 0.1–4 ml/g, more preferably of 0.1–3 ml/g and most preferably of 0.1–2 ml/g determined by nitrogen adsorption. Pores with a diameter smaller than 1 nm are generally not present in conventional hydrotreating catalysts. Further, conventional hydrotreating catalysts have generally a surface area of at least 10 $m^2$/g and more preferably of at least 50 $m^2$/g and most preferably of at least 100 $m^2$/g, determined via the B.E.T. method. For instance, nickel carbonate can be chosen which has a total pore volume of 0.19–0.39 ml/g and preferably of 0.24–0.35 ml/g determined by nitrogen adsorption and a surface area of 150–400 $m^2$/g and more preferably of 200–370 $m^2$/g determined by the B.E.T. method. Furthermore these metal components should have a median particle diameter of at least 50 nm, more preferably at least 100 nm, and preferably not more than 5000 μm and more preferably not more than 3000 μm. Even more preferably, the median particle diameter lies in the range of 0.1–50 μm and most preferably in the range of 0.5–50 μm. For instance, by choosing a metal component which is added at least partly in the solid state and which has a large median particle diameter, the other metal components will only react with, the outer layer of the large metal component particle. In this case, so-called "core-shell" structured bulk catalyst particles are obtained.

An appropriate morphology and texture of the metal component can either be achieved by applying suitable preformed metal components or by preparing these metal components by the above-described precipitation under such conditions that a suitable morphology and texture is obtained. A proper selection of appropriate precipitation conditions can be made by routine experimentation.

As has been set out above, to retain the morphology and texture of the metal components which are added at least partly in the solid state, it is essential that the metal of the metal component at least partly remains in the solid state during the whole process of this solid route. It is noted again that it is essential that in no case should the amount of solid metals during the process of the solid route becomes zero. The presence of solid metal comprising particles can easily be detected by visual inspection at least if the diameter of the solid particles in which the metals are comprised is larger than the wavelength of visible light. Of course, methods such as quasi-elastic light scattering (QELS) or near forward scattering which are known to the skilled person can also be used to ensure that in no point in time of the process of the solid route, all metals are in the solute state.

The protic liquid to be applied in the solid or solution route of this invention for preparing catalyst can be any protic liquid. Examples include water, carboxylic acids, and alcohols such as methanol or ethanol. Preferably, a liquid comprising water such as mixtures of an alcohol and water and more preferably water is used as protic liquid in this solid route. Also different protic liquids can be applied simultaneously in the solid route. For instance, it is possible to add a suspension of a metal component in ethanol to an aqueous solution of another metal component.

The Group VIB metal generally comprises chromium, molybdenum, tungsten, or mixtures thereof Suitable Group VIII non-noble metals are, e.g., iron, cobalt, nickel, or mixtures thereof. Preferably, a combination of metal components comprising nickel, molybdenum and tungsten or nickel, cobalt, molybdenum and tungsten is applied in the process of the solid route. If the protic liquid is water, suitable nickel components which are at least partly in the solid state during contacting comprise water-insoluble nickel components such as nickel carbonate, nickel hydroxide, nickel phosphate, nickel phosphite, nickel formate, nickel sulfide, nickel molybdate, nickel tungstate, nickel oxide, nickel alloys such as nickel-molybdenum alloys, Raney nickel, or mixtures thereof. Suitable molybdenum components, which are at least partly in the solid state during contacting, comprise water-insoluble molybdenum components such as molybdenum (di- and tri) oxide, molybdenum carbide, molybdenum nitride, aluminum molybdate, molybdic acid (e.g. $H_2MoO_4$), molybdenum sulfide, or mixtures thereof. Finally, suitable tungsten components which are at least partly in the solid state during contacting comprise tungsten di- and trioxide, tungsten sulfide ($WS_2$ and $WS_3$), tungsten carbide, tungstic acid (e.g. $H_2WO_4 \cdot H_2O$, $H_2W_4O_{13} \cdot 9H_2O$), tungsten nitride, aluminum tungstate (also meta-, or polytungstate) or mixtures thereof. These components are generally commercially available or can be prepared by, e.g., precipitation. e.g., nickel carbonate can be prepared from a nickel chloride, sulfate, or nitrate solution by adding an appropriate amount of sodium carbonate. It is generally known to the skilled person to choose the precipitation conditions in such a way as to obtain the desired morphology and texture.

In general, metal components, which mainly contain C, O, and/or H besides the metal, are preferred because they are less detrimental to the environment. Nickel carbonate is a preferred metal component to be added at least partly in the solid state because when nickel carbonate is applied, $CO_2$ evolves and positively influences the pH of the reaction mixture. Further, due to the transformation of carbonate into $CO_2$, the carbonate does not end up in the wastewater.

Preferred nickel components which are added in the solute state are water-soluble nickel components, e.g. nickel nitrate, nickel sulfate, nickel acetate, nickel chloride, or mixtures thereof. Preferred molybdenum and tungsten components which are added in the solute state are water-soluble molybdenum and tungsten components such as alkali metal or ammonium molybdate (also peroxo-, di-, tri-, tetra-, hepta-, octa-, or tetradecamolybdate), Mo—P heteropolyanion compounds, Wo—Si heteropolyanion compounds, W—P heteropolyanion compounds, W—Si heteropolyanion compounds, Ni—Mo—W heteropolyanion compounds, Co—Mo—W heteropolyanion compounds, alkali metal or ammonium tungstates (also meta-, para-, hexa-, or polytungstate), or mixtures thereof.

Preferred combinations of metal components are nickel carbonate, tungstic acid and molybdenum oxide. Another preferred combination is nickel carbonate, ammonium dimolybdate and ammonium metatungstate. It is within the scope of the skilled person to select further suitable combinations of metal components. It must be noted that nickel carbonate always comprises a certain amount of hydroxy-groups. It is preferred that the amount of hydroxy-groups present in the nickel carbonate be high.

An alternative method of preparing the catalysts used in the practice of the present invention is to prepare the bulk catalyst composition by a process comprising reacting in a reaction mixture a Group VIII non-noble metal component in solution and a Group VIB metal component in solution to obtain a precipitate. As in the case of the solid route, preferably, one Group VIII non-noble metal component is reacted with two Group VIB metal components. The molar ratio of Group VIB metals to Group VIII non-noble metals applied in the process of the solution route is preferably the same as described for the solid route. Suitable Group VIB and Group VIII non-noble metal components are, e.g., those water-soluble nickel, molybdenum and tungsten components described above for the solid route. Further Group VIII non-noble metal components are, e.g., cobalt or iron components. Further Group VIB metal components are, e.g. chromium components. The metal components can be added to the reaction mixture in solution, suspension or as such. If soluble salts are added as such, they will dissolve in the reaction mixture and subsequently be precipitated. Suitable Group VIB metal salts which are soluble in water are ammonium salts such as ammonium dimolybdate, ammonium tri-, tetra- hepta-, octa-, and tetradeca- molybdate, ammonium para-, meta-, hexa-, and polytungstate, alkali metal salts, silicic acid salts of Group VIB metals such as molybdic silicic acid, molybdic silicic tungstic acid, tungstic acid, metatungstic acid, pertungstic acid, heteropolyanion compounds of Mo—P, Mo—Si, W—P, and W—Si. It is also possible to add Group VIB metal-containing compounds which are not in solution at the time of addition, but where solution is effected in the reaction mixture. Examples of these compounds are metal compounds which contain so much crystal water that upon temperature increase they will dissolve in their own metal water. Further, non-soluble metal salts may be added in suspension or as such, and solution is effected in the reaction mixture. Suitable non-soluble metals salts are heteropolyanion compounds of Co—Mo—W (moderately soluble in cold water), heteropolyanion compounds of Ni—Mo—W (moderately soluble in cold water).

The reaction mixture is reacted to obtain a precipitate. Precipitation is effected by adding a Group VIII non-noble metal salt solution at a temperature and pH at which the Group VIII non-noble metal and the Group VIB metal precipitate, adding a compound which complexes the metals and releases the metals for precipitation upon temperature increase or pH change or adding a Group VIB metal salt solution at a temperature and pH at which the Group VIII non-noble metal and Group VIB metal precipitate, changing the temperature, changing the pH, or lowering the amount of the solvent. The precipitate obtained with this process appears to have high catalytic activity. In contrast to the conventional hydroprocessing catalysts, which usually comprise a carrier impregnated with Group VIII non-noble metals and Group VIB metals, said precipitate can be used without a support. Unsupported catalyst compositions are usually referred to as bulk catalysts. Changing the pH can be done by adding base or acid to the reaction mixture, or adding compounds, which decompose upon temperature, increase into hydroxide ions or $H^+$ ions that respectively increase or decrease the pH. Examples of compounds that decompose upon temperature increase and thereby Increase or decrease the pH are urea, nitrites, ammonium cyanate, ammonium hydroxide, and ammonium carbonate.

In an illustrative process according to the solution route, solutions of ammonium salts of a Group VIB metal are made and a solution of a Group VIII non-noble metal nitrate is made. Both solutions are heated to a temperature of approximately 90° C. Ammonium hydroxide is added to the Group VIB metal solution. The Group VIII non-noble metal solution is added to the Group VIB metal solution and direct precipitation of the Group VIB and Group VIII non-noble metal components occurs. This process can also be conducted at lower temperature and/or decreased pressure or higher temperature and/or increased pressure.

In another illustrative process according to the solution route, a Group VIB metal salt, a Group VIII metal salt, and ammonium hydroxide are mixed in solution together and heated so that ammonia is driven off and the pH is lowered to a pH at which precipitation occurs. For instance when nickel, molybdenum, and tungsten components are applied, precipitation typically occurs at a pH below 7.

Independently from whether the solid or solution route is chosen in step (i), the resulting bulk catalyst composition preferably comprises and more preferably consists essentially of bulk catalyst particles having the characteristics of the bulk catalyst particles described under the heading "Catalyst compositions of the invention."

The bulk catalyst composition can generally be directly shaped into hydroprocessing particles. If the amount of liquid of the bulk catalyst composition is so high that it cannot be directly subjected to a shaping step, a solid liquid separation can be performed before shaping. Optionally the bulk catalyst composition, either as such or after solid liquid separation, can be calcined before shaping.

The median diameter of the bulk catalyst particles is at least 50 nm, more preferably at least 100 nm, and preferably not more than 5000 $\mu$m and more preferably not more than 3000 $\mu$m. Even more preferably, the median particle diameter lies in the range of 0.1–50 $\mu$m and most preferably in the range of 0.5–50 $\mu$m.

If a binder material is used in the preparation of the catalyst composition it can be any material that is conventionally applied as a binder in hydroprocessing catalysts. Examples include silica, silica-alumina, such as conventional silica-alumina, silica-coated alumina and alumina-coated silica, alumina such as (pseudo) boehmite, or gibbsite, titania, zirconia, cationic clays or anionic clays such as saponite, bentonite, kaoline, sepiolite or hydrotalcite, or mixtures thereof. Preferred binders are silica, silica-alumina, alumina, titanic, zirconia, or mixtures thereof. These binders may be applied as such or after peptization. It is also possible to apply precursors of these binders that, during the process of the invention are converted into any of the above-described binders. Suitable precursors are, e g., alkali metal aluminates (to obtain an alumina binder), water glass (to obtain a silica binder), a mixture of alkali metal aluminates and water glass (to obtain a silica alumina binder), a mixture of sources of a di-, tri-, and/or tetravalent metal such as a mixture of water-soluble salts of magnesium, aluminum and/or silicon (to prepare a cationic clay and/or anionic clay), chlorohydrol, aluminum sulfate, or mixtures thereof.

If desired, the binder material may be composited with a Group VIB metal and/or a Group VIII non-noble metal, prior to being composited with the bulk catalyst composition and/or prior to being added during the preparation thereof. Compositing the binder material with any of these metals may be carried out by impregnation of the solid binder with these materials. The person skilled in the art knows suitable impregnation techniques. If the binder is peptized, it is also possible to carry out the peptization in the presence of Group VIB and/or Group VIII non-noble metal components.

If alumina is applied as binder, the surface area preferably lies in the range of 100–400 m$^2$/g, and more preferably 150–350 m$^2$/g, measured by the B.E.T. method. The pore volume of the alumina is preferably in the range of 0.5–1.5 ml/g measured by nitrogen adsorption.

Generally, the binder material to be added in the process of the invention has less catalytic activity than the bulk catalyst composition or no catalytic activity at all. Consequently, by adding a binder material, the activity of the bulk catalyst composition may be reduced. Therefore, the amount of binder material to be added in the process of the invention generally depends on the desired activity of the final catalyst composition. Binder amounts from 0–95 wt. % of the total composition can be suitable, depending on the envisaged catalytic application. However, to take advantage of the resulting unusual high activity of the composition of the present invention, binder amounts to be added are generally in the range of 0.5–75 wt. % of the total composition.

The catalyst composition can be directly shaped. Shaping comprises extrusion, pelletizing, beading, and/or spray drying. It must be noted that if the catalyst composition is to be applied in slurry type reactors, fluidized beds, moving beds, expanded beds, or ebullating beds, spray drying or beading is generally applied for fixed bed applications, generally, the catalyst composition is extruded, pelletized and/or beaded. In the latter case, prior to or during the shaping step, any additives that are conventionally used to facilitate shaping can be added. These additives may comprise aluminum stearate, surfactants, graphite or mixtures thereof. These additives can be added at any stage prior to the shaping step. Further, when alumina is used as a binder, it may be desirable to add acids prior to the shaping step such as nitric acid to increase the mechanical strength of the extrudates.

It is preferred that a binder material is added prior to the shaping step. Further, it is preferred that the shaping step is carried out in the presence of a liquid, such as water. Preferably, the amount of liquid in the extrusion mixture, expressed as LOI is in the range of 20–80%.

The resulting shaped catalyst composition can, after an optional drying step, be optionally calcined. Calcination however is not essential to the process of the invention. If a calcination is carried out in the process of the invention, it can be done at a temperature of, e.g., from 100°–600° C. and preferably 350° to 500° C. for a time varying from 0 5 to 48 hours. The drying of the shaped particles is generally carried out at temperatures above 100° C.

In a preferred embodiment of the invention, the catalyst composition is subjected to spray drying, (flash) drying, milling, kneading, or combinations thereof prior to shaping. These additional process steps can be conducted either before or after a binder is added, after solid-liquid separation, before or after calcination and subsequent to re-wetting. It is believed that by applying any of the above-described techniques of spray drying, (flash) drying, milling, kneading, or combinations thereof, the degree of mixing between the bulk catalyst composition and the binder material is improved. This applies to both cases where the binder material is added before or after the application of any of the above-described methods. However, it is generally preferred to add the binder material prior to spray drying and/or any alternative technique. If the binder is added subsequent to spray drying and/or any alternative technique, the resulting composition is preferably thoroughly mixed by any conventional technique prior to shaping. An advantage of, e.g., spray drying is that no wastewater streams are obtained when this technique is applied.

Furthermore, a cracking component may be added during catalyst preparation. A cracking component in the sense of the present invention is any conventional cracking component such as cationic clays, anionic clays, zeolites such as ZSM-5, (ultra-stable) zeolite Y. zeolite X, ALPO's, SAPO's, amorphous cracking components such as silica-alumina, or mixtures thereof. It will be clear that some materials may act as a binder and a cracking component at the same time. For instance, silica-alumina may have at the same time a cracking and a binding function.

If desired, the cracking component may be composited with a Group VIB metal and/or a Group VIII non-noble metal prior to being composited with the bulk catalyst composition and/or prior to being added during the preparation thereof. Compositing the cracking component with any of these metals may be carried out by impregnation of the cracking component with these materials.

The cracking component, which can comprise about 0–80 wt. %, based on the total weight of the catalyst, can be added at any stage of the process of the present invention prior to the shaping step. However, it is preferred to add the cracking component during the compositing step (ii) with the binder.

Generally, it depends on the envisaged catalytic application of the final catalyst composition which of the above-described cracking components is added. A zeolite is preferably added if the resulting composition shall be applied in hydrocracking or fluid catalytic cracking. Other cracking components such as silica-alumina or cationic clays are preferably added if the final catalyst composition shall be used in hydrotreating applications. The amount of cracking material that is added depends on the desired activity of the final composition and the application envisaged and thus may vary from 0–80 wt. %. based on the total weight of the catalyst composition.

If desired, further materials can be added in addition to the metal components already added. These materials include any material that is added during conventional hydroprocessing catalyst preparation. Suitable examples are phosphorus compounds, boron compounds, fluorine-containing compounds, additional transition metals, rare earth metals, fillers, or mixtures thereof.

Suitable phosphorus compounds include ammonium phosphate, phosphoric acid, or organic phosphorus compounds. Phosphorus compounds can be added at any stage of the process of the present invention prior to the shaping step and/or subsequent to the shaping step. If the binder material is peptized, phosphorus compounds can also be used for peptization. For instance, the binder can be peptized by contacting the binder with phosphoric acid or with a mixture of phosphoric and nitric acid.

Suitable additional transition metals are, e.g., rhenium, ruthenium, rhodium, iridium, chromium, vanadium, iron, cobalt, platinum, palladium, cobalt, nickel, molybdenum, or tungsten. Nickel, molybdenum , and tungsten can be applied in the form of any of the water-insoluble nickel, molybdenum and/or tungsten components that are described above for the solid route. These metals can be added at any stage of the process of the present invention prior to the shaping step. Apart from adding these metals during the process of the invention, it is also possible to composite the final catalyst composition therewith. It is, e.g., possible to impregnate the final catalyst composition with an impregnation solution comprising any of these metals.

The processes of the present invention for preparing the bulk catalyst compositions may further comprise a sulfidation step. Sulfidation is generally carried out by contacting the catalyst composition or precursors thereof with a sulfur containing compound such as elementary sulfur, hydrogen sulfide or polysulfides. The sulfidation can generally be carried out subsequently to the preparation of the bulk catalyst composition but prior to the addition of a binder material, and/or subsequently to the addition of the binder material but prior to subjecting the catalyst composition to spray drying and/or any alternative method, and/or subsequently to subjecting the composition to spray drying and/or any alternative method but prior to shaping, and/or subsequently to shaping the catalyst composition. It is preferred that the sulfidation is not carried out prior to any process step that reverts the obtained metal sulfides into their oxides. Such process steps are, e.g., calcination or spray drying or any other high temperature treatment in the presence of oxygen. Consequently, if the catalyst composition is subjected to spray drying and/or any alternative technique, the sulfidation should be carried out subsequent to the application of any of these methods.

Additionally to, or instead of, a sulfidation step, the bulk catalyst composition may be prepared from at least one metal sulfide. If, e.g ,the solid route is applied the bulk catalyst component can be prepared form nickel sulfide and/or molybdenum sulfide and/or tungsten sulfide.

If the catalyst composition is used in a fixed bed processes, the sulfidation is preferably carried out subsequent to the shaping step and, if applied, subsequent to the last calcination step. Preferably, the sulfidation is carried out ex situ, i.e., the sulfidation is carried out in a separate reactor prior to loading the sulfided catalyst composition into the hydroprocessing unit. Furthermore, it is preferred that the catalyst composition is both sulfided ex situ and in situ.

The catalyst compositions used in the practice of the present invention are represented by the formula:

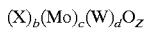

wherein X is one or more a Group VIII non-noble metal, the molar ratio of b: (c+d) is 0.5/1 to 3/1, preferably 0.75/1 to 1.5/1, more preferably 0.75/1 to 1.25/1;

The molar ratio of c:d is preferably >0.01/1, more preferably >0.1/1, still more preferably 1/10 to 10/1, still more preferably 1/3 to 3/1, most preferably substantially equimolar amounts of Mo and W, e.g., 2/3 to 3/2; and z=[2b+6(c+d)]/2.

The essentially amorphous material has a unique X-ray diffraction pattern showing crystalline peaks at d=2.53 Angstroms and d=1.70 Angstroms.

The mixed metal oxide is readily produced by the decomposition of a precursor having the formula:

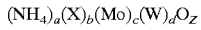

wherein the molar ratio of a:b is $\leq 1.0/1$, preferably 0–1; and b, c, and d, are as defined above, and z=[a+2b+6(c+d)]/2. The precursor has similar peaks at d=2.53 and 1.70 Angstroms.

Decomposition of the precursor may be effected at elevated temperatures, e.g., temperatures of at least about 300° C., preferably about 300–450° C., in a suitable atmosphere, e.g., inerts such as nitrogen, argon, or steam, until decomposition is substantially complete, i.e., the ammonium is substantially completely driven off. Substantially complete decomposition can be readily established by thermogravimetric analysis (TGA), i.e., flattening of the weight change curve.

It has been found that in this case, the bulk catalyst particles are sintering-resistant. Thus the active surface area of the bulk catalyst particles is maintained during use. The molar ratio of Group VIB to Group VIII non-noble metals ranges generally from 10:1–1:10 and preferably from 3:1–1:3. In the case of a core-shell structured particle, these ratios of course apply to the metals contained in the shell. If more than one Group VIB metal is contained in the bulk catalyst particles, the ratio of the different Group VIB metals is generally not critical. The same holds when more than one Group VIII non-noble metal is applied. In the case where molybdenum and tungsten are present as Group VIB metals, the molybenum:tungsten ratio preferably lies in the range of 9:1–1:9. Preferably the Group VIII non-noble metal comprises nickel and/or cobalt. It is further preferred that the Group VIB metal comprises a combination of molybdenum and tungsten. Preferably, combinations of nickel/molybdenum/tungsten and cobalt/molybdenum/tungsten and nickel/cobalt/molybdenum/tungsten are used. These types of precipitates appear to be sinter-resistant. Thus, the active surface area of the precipitate is remained during use. The metals are preferably present as oxidic compounds of the corresponding metals, or if the catalyst composition has been sulfided, sulfidic compounds of the corresponding metals.

Preferably the particles have a surface area of at least 50 m$^2$/g and more preferably of at least 100 m$^2$/g measured via the B.E.T. method. It is furthermore preferred that the particles comprise 50–100 wt. %, and even more preferably 70–100 wt. % of at least one Group VIII non-noble metal and at least one Group VIB metal, based on the total weight of the particles, calculated as metal oxides. The amount of Group VIB and Group VIII non-noble metals can easily be determined via TEM-EDX.

It is desired that the pore size distribution of the particles is approximately the same as the one of conventional hydrotreating catalysts. More in particular, these particles have preferably a pore volume of 0.05–5 ml/g, more preferably of 0.1–4 ml/g, still more preferably of 0.1–3 ml/g and most preferably 0.1–2 ml/g determined by nitrogen adsorption. Preferably, pores smaller than 1 nm are not present. Furthermore these particles preferably have a median diameter of at least 50 nm, more preferably at least 100 nm, and preferably not more than 5000 μm and more preferably not more than 3000 μm. Even more preferably, the median particle diameter lies in the range of 0.1–50 μm and most preferably in the range of 0 5–50 μm.

It was found that the bulk catalyst particles have a characteristic X-ray diffraction pattern which differs from catalysts obtained by co-mixing and conventional hydroprocessing catalysts obtained by impregnation. The X-ray diffraction pattern of the bulk catalyst particles comprises, and preferably essentially consists of, peaks characteristic to the reacted metal components. If, e.g., nickel hydroxy-carbonate has been contacted with a molybdenum and tungsten component as described above, the resulting bulk catalyst particles are characterized by an X-ray diffraction pattern which comprises peaks at d values of(4.09 Å), 2.83 Å, 2.53 Å, 2.32 Å, 2.23 Å, 1.70 Å, (1.54 Å), 1.47 Å. Values in brackets indicate that the corresponding peaks are rather broad and/or have a low intensity or are not distinguished at all. The term "the X-ray diffraction pattern essentially consists of" these peaks means that apart from these peaks, there are essentially no further peaks contained in the diffraction pattern. The precipitate for catalyst obtained by the solution route has a characteristic X-ray diffraction pattern which differs from catalyst obtained by co-mixing and conventional hydroprocessing catalysts obtained by impregnation. For instance the X-ray diffraction pattern of a Ni—Mo—W precipitate as prepared by the solution route has peaks at d values of 2.52 Å, 1.72 Å and 1.46 Å.

Also as previously stated, the catalyst composition may comprise conventional hydroprocessing catalysts. The binder materials and cracking components of the conventional hydroprocessing catalyst generally comprise any of the above-described binder materials and cracking components. The hydrogenation metals of the conventional hydroprocessing catalyst generally comprise Group VIB and Group VIII non-noble metals such as combinations of nickel or cobalt with molybdenum or tungsten. Suitable conventional hydroprocessing catalysts are, e.g., hydrotreating catalysts. These catalysts can be in the spent, regenerated, or fresh state.

The surface area of the catalyst composition preferably is at least 40 m$^2$/g, more preferably at least 80 m$^2$/g and most preferably at least 120 m$^2$/g. The total pore volume of the catalyst composition is preferably at least 0.05 ml/g and more preferably at least 0.01 ml/g as determined by water porosimetry. To obtain catalyst compositions with high mechanical strength, it may be desirable that the catalyst composition of the invention has a low macroporosity.

As will be clear from the above, it is possible to add the Group VIII non-noble metal containing compound and the Group VIB metal-containing compound in various ways, at various temperatures and pHs, in solution, in suspension, and as such, simultaneously and sequentially.

The precursor compound can also be readily prepared by one of several methods, including a variation of the boiling decomposition method used by Teichner and Astier in which a tungsten compound is added to the initial mixture of a molybdenum salt, a nickel salt and ammonium hydroxide. Direct precipitation and pH controlled precipitation may also be used to prepare the precursor compound. In all cases, however, water soluble salts of nickel, molybdenum and tungsten are employed.

In another embodiment, a binder can be added to the bulk mixed metal oxide to maintain particle integrity. The binder can be silica, alumina, silica-alumina or other materials generally known as particle binders. When utilizing a binder, the amount may range from about 1–30 wt % of the finished catalyst, preferably about 5–26 wt % of the finished catalyst.

After recovering the precursor product, regardless of preparation method, the precursor is decomposed at temperatures ranging from about 300–450° C. in a suitably inert or air atmosphere.

The decomposed precursor can be sulfided or pre-sulfided by a variety of known methods. For example, the decomposition product can be contacted with a gas comprising H$_2$S and hydrogen, e.g., 10% H$_2$S/H$_2$, at elevated temperatures for a period of time sufficient to sulfide the decomposition product, usually at the point of H$_2$S breakthrough in the exit gas. Sulfiding can also be effected, in situ, by passing a typical feedstock containing sulfur over the decomposition product.

Process conditions applicable for the use of the catalysts described herein may vary widely depending on the feedstock to be treated. Thus, as the boiling point of the feed increases, the severity of the conditions will also increase. The following table serves to illustrate typical conditions for a range of feeds.

| FEED | TYPICAL BOILING RANGE ° C. | TEMP. ° C. | PRESS, BAR | SPACE VELOCITY V/V/HR | H$_2$ GAS RATE SCF/3 |
|---|---|---|---|---|---|
| naphtha | 25–210 | 100–370 | 10–60 | 0.5–10 | 100–2,000 |
| diesel | 170–350 | 200–400 | 15–110 | 0.5–4 | 500–6,000 |
| heavy gas oil | 325–475 | 260–430 | 15–170 | 0.3–2 | 1000–6,000 |
| lube oil | 290–550 | 200–450 | 6–210 | 0.2–5 | 100–10,000 |
| residuum | 10–50%>575 | 340–450 | 65–1100 | 0.1–1 | 2,000–10,000 |

While the invention described herein shows enhanced activity for hydrodenitrogenation, most HDN catalysts will also show hydrodesulfurization (HDS) activity. Consequently, the catalysts and processes described herein will be useful on feeds containing both nitrogen and sulfur, and will be particularly useful on feeds high in nitrogen.

The following examples will serve to illustrate, but not limit, this invention.

EXAMPLE 1

Preparation of $NH_4$—Ni—Mo—O Phase (Boiling Decomposition as per Teichner and Astier Procedure)

In a 1 liter flask, 26.5 g ammonium molybdate (0.15 moles Mo) and 43.6 g nickel nitrate hexahydrate (0.15 moles Ni) were dissolved in 300 cc of water so that the resulting pH equaled 4.3. To this solution, a concentrated $NH_4OH$ solution was added. At first, a precipitate formed which on further addition of $NH_4OH$ dissolved to give a clear blue solution with a pH of 8.3, and additional $NH_4OH$ (~250 cc) was added until a pH of 10 was reached. The solution was heated to 90° C. for 3 h during which ammonia gas evolved and a green precipitate formed. The final pH lay between 6.8 and 7. The suspension was cooled to room temperature, filtered, washed with water and dried at 120° C. overnight. About 18.6 g of material was obtained. The sample analyzed for Ni at 26.6 wt. % and Mo at 34 wt. %. The X-ray diffraction spectra of the phase matches the pattern reported by Teichner and Astier.

EXAMPLE 2

Preparation of NH4—Ni—$Mo_{0.5}W_{0.5}$—O by Boiling Decomposition

In a 1 liter flask, 13.2 g ammonium molybdate (0.075 moles Mo), 18.7 g ammonium metatungstate (0.075 moles W) and 43.6 g nickel nitrate hexahydrate (0.15 moles Ni) were dissolved in 300 cc of water so that the resulting pH equaled 4.3. To this solution, a concentrated $NH_4OH$ solution (~600 cc) was added until the pH reached 10. At this point, some precipitate remained. The solution was refluxed at ~100° C. for 3 h. During this heating, the precipitate dissolved to give a clear blue solution and on further heating, a green precipitate formed. The heating was continued until the pH reached between 6.8 and 7. The suspension was cooled to room temperature, filtered, washed with water and dried at 120° C. overnight. 18 grams of material is obtained. The X-ray diffraction spectra of the phase is given in FIG. 1 showing an amorphous background with the two largest peaks at d=2.53 and 1.70Å.

EXAMPLE 3

Preparation of $NH_4$—Ni—$Mo_{0.5}W_{0.5}$—O by direct precipitation

In a 1 liter flask, 17.65 g of ammonium molybdate (0.1 mole Mo) and 24.60 g of ammonium metatungstate (0.1 mole W) were dissolved in 800 cc of water giving a solution pH of ~5.2. To this solution 0.4 moles of $NH_4OH$ (~30 cc) was added, raising the pH to ~9.8 (solution A). This solution was warmed to 90° C. A second solution was prepared by adding 58.2 g of nickel nitrate, (0.2 moles Ni) which was dissolved in 50 cc of water (solution B) and maintained at 90° C. This solution was added dropwise at a rate of 7 cc/min into the ammonium molybdate/ammonium meta- tungstate solution. A precipitate begins to form after ¼ of the solution was added. This suspension which was at a pH ~6.5 was stirred for 30 minutes while the temperature was maintained at 90° C. The material was filtered hot, washed with hot water, and dried at 120° C. Approximately 38 g of material was recovered.

EXAMPLE 4

Preparation of $NH_4$—Ni—$Mo_{0.5}$—$Mo_{0.5}$—O by Controlled pH Precipitation

Two solutions were prepared with the same amounts of nickel, tungsten, molybdenum and ammonium hydroxide are described in Example 3 (solutions A and B) except that each solution contained about 700 cc of water. The two solutions were added into a separate vessel initially containing 400 cc of water held at 90° C. Solution B (the acidic solution) was pumped into the vessel at a constant rate of ~15 cc/min, while solution A is added through a separate pump which is under feedback PC control and set to maintain the pH at 6.5. On mixing the two solutions a precipitate forms. The slurry was stirred at 90° C. for 30 minutes, filtered hot, washed with hot water, and dried at 120° C.

EXAMPLE 5

Catalytic Evaluation Using Dibenzothiophene (DBT)

1.5–2 g of the catalysts of Examples 1–4 were placed in a quartz boat which was in turn inserted into a horizontal quartz tube and placed into a Lindberg furnace. The temperature was raised to 370° C. in about one hour with $N_2$ flowing at 50 cc/m, and the flow continued for 1.5 h at 370° C. $N_2$ was switched off and 10% $H_2S/H_2$ then added to the reactor at 20 cc/m, the temperature increased to 400° C., and held there for 2 hours. The heat was then shut off and the catalyst cooled in flowing $H_2S/H_2$ to 70° C., at which point this flow was discontinued and $N_2$ was added. At room temperature, the quartz tube was removed and the material transferred into a $N_2$ purged glove box. Catalysts were evaluated in a 300 cc modified Carberry batch reactor designed for constant hydrogen flow. The catalyst was pilled and sized to 20/40 mesh and one gram was loaded into a stainless steel basket, sandwiched between a layer of mullite beads. 100 cc of liquid feed, containing 5 wt % dibenzothiophene in decalin was added to the autoclave. A hydrogen flow of 100 cc/min was passed through the reactor and the pressure was maintained at 3150 kPa using a back pressure regulator. The temperature was raised to 350° C. at 5–6 deg/min and run until either 50% DBT was converted or until 7 hours was reached. A small aliquot of product was removed every 30 minutes and analyzed by GC. Rate constants for the overall conversion as well as the conversion to the reaction products biphenyl (BP) and cyclohexylbenzene (CHB) were calculated as described by M. Daage and R. R. Chianelli [J. Cat. 149, 414–27 (1994)] and are shown in Table 1. As described in that article, high selectivities to cyclohexylbenzene relative to BP during the desulfurization reaction are a good indication of a catalyst with high hydrodenitrogenation activity, whereas high selectivities of BP relative to CHB indicates a catalyst with high hydrodesulfurization activity.

The results show that partial substitution of tungsten for molybdenum results in catalysts that are substantially higher for DBT conversion. A standard supported Ni-Mo on $Al_2O_3$ catalyst is also shown for comparison. The high CHB/BP ratio suggests that the catalysts are active for HDN.

TABLE 1

Comparison of Activity in DBT Conversion Tests With Tungsten Addition by Different Preparation Schemes

| catalyst | preparation technique | example # | $K_{total}$ @ 350° C. | CHB/BP @ 350° C. |
|---|---|---|---|---|
| $NH_4$—Ni—Mo—O | boiling decomposition | 1 | 106 | 10.4 |
| $NH_4$—Ni—$Mo_{.5}W_{.5}$—O | boiling decomposition | 2 | 171 | 10.2 |
| $NH_4$—Ni—$Mo_{.5}W_{.5}$—O | direct precipitation | 3 | 167 | 12.4 |
| $NH_4$—Ni—$Mo_{.5}W_{.5}$—O | controlled pH preparation | 4 | 181 | 12.0 |
| $Ni,Mo/Al_2O_3$ | impregnation | | 129 | 6.4 |

EXAMPLE 6

A series of catalysts were prepared in accordance with the general preparation scheme of example 2 (i.e., boiling decomposition) but varying the Mo and W relative ratios by changing the amount of ammonium molybdate and ammonium metatungstate added to the solutions. Decomposition was effected as described in Example 5. The catalysts so prepared are shown in Table 2 along with their catalytic activities for DBT measured as described in Example 5.

TABLE 2

Comparison of Activity in DBT Conversion Tests with Variation in Relative W and Mo Content

| Catalyst | Sample | ammonium molybdate (g) | ammonium metatungstate (g) | nickel nitrate hexahydrate (g) | $K_{total}$ @ 350° C. | CHB/BP @ 350° C. |
|---|---|---|---|---|---|---|
| $NH_4$—NiW—O | 18983-97 | 0 | 36.95 | 43.62 | 128 | 11.3 |
| $NH_4$—$NiMo_{.1}W_{.9}$—O | 18983-125 | 2.65 | 33.62 | 43.62 | 132 | 14.1 |
| $NH_4$—$NiMo_{.3}W_{.7}$—O | 18983-101 | 7.94 | 25.87 | 43.62 | 154 | 11.6 |
| $NH_4$—$NiMo_{.5}W_{.5}$—O | 18357-109 | 13.17 | 18.74 | 43.62 | 171 | 10.2 |
| $NH_4$—$NiMo_{.7}W_{.3}$—O | 18983-95 | 18.54 | 11.09 | 43.62 | 158 | 11.5 |
| $NH_4$—$NiMo_{.9}W_{.1}$—O | 18983-92 | 23.83 | 3.69 | 43.62 | 141 | 10.5 |

The data show that the most active catalyst contains an approximately equimolar mixture of tungsten and molybdenum.

Example 7

A series of catalysts were prepared as described in Example 3 (direct precipitation) in which equimolar mixtures of Mo and W were precipitated but the nickel content was varied. Decomposition was effected as described in EXAMPLE 5. The catalysts so prepared are shown in Table 3 along with their catalytic activities for DBT measured as described in example 5.

TABLE 3

Variation of Nickel Content in $NH_4$—Ni—$Mo_{.5}W_{.5}$—O Catalysts

| Catalyst | Sample | ammonium molybdate (g) | ammonium metatungstate (g) | nickel nitrate hexahydrate (g) | $K_{total}$ @ 350° C. | CHB/BP @ 350° C. |
|---|---|---|---|---|---|---|
| $NH_4$—$Ni_{0.75}Mo_{.5}W_{.5}$—O | 19086-110 | 17.65 | 24.6 | 43.65 | 171 | 13.0 |
| $NH_4$—$Ni_{1.0}Mo_{.5}W_{.5}$—O | 19086-82 | 17.65 | 24.6 | 58.2 | 167 | 12.4 |

TABLE 3-continued

Variation of Nickel Content in $NH_4$—Ni—$Mo_{.5}W_{.5}$—O Catalysts

| Catalyst | Sample | ammonium molybdate (g) | ammonium metatungstate (g) | nickel nitrate hexahydrate (g) | $K_{total}$ @ 350° C. | CHB/BP @ 350° C. |
|---|---|---|---|---|---|---|
| $NH_4$—$Ni_{1.25}Mo_{.5}W_{.5}$—O | 19086-111 | 17.65 | 24.6 | 72.75 | 174 | 11.0 |
| $NH_4$—$Ni_{1.5}Mo_{.5}W_{.5}$—O | 19086-112 | 17.65 | 24.6 | 87.3 | 148 | 9.55 |

Catalytic performance does not change substantially with variations in Ni from 0.75 to 1.5, although K appears to go through a maximum at about 1.25 Ni.

EXAMPLE 8

A series of catalysts were prepared in which the quantity of $NH_4OH$ used in the preparation was varied. The catalysts were prepared in accordance to the procedure described in Example 3 except that the amount of $NH_4OH$ in solution A was varied to change to $NH_4OH$/Ni molar ratio when the two solutions were mixed. Decomposition was effected as described in Example 5. The catalysts so prepared are shown in Table 4 along with their catalytic activities for DBT measured as described in Example 5.

TABLE 4

Variation in $NH_4OH$ Addition to Preparation

| Catalyst $NH_4OH$/Ni mole ratio | Sample | ammonium molybdate (g) | ammonium metatungstate (g) | nickel nitrate hexahydrate (g) | $cm^3$ conc $NH_4OH$ | $K_{total}$ @ 350° C. | $K_{CHB/BP}$ @ 350° C. |
|---|---|---|---|---|---|---|---|
| 1:2 | 19086-96 | 17.65 | 24.6 | 43.65 | 6.8 | 102 | 10.5 |
| 1:1 | 19086-97 | 17.65 | 24.6 | 58.2 | 14 | 137 | 10.4 |
| 2:1 | 19086-82 | 17.65 | 24.6 | 72.75 | 30 | 167 | 12.4 |
| 3:1 | 19086-104 | 17.65 | 24.6 | 87.3 | 41 | 164 | 11.4 |
| 4:1 | 19086-106 | 17.65 | 24.6 | 87.3 | 55 | 161 | 12.1 |

While decomposition of the precursor compound will drive off most, if not all, of the ammonium portion of the precursor, the preparation of the precursor and the catalytic utility of the decomposition product can be affected by the amount of $NH_4OH$ employed. Thus, the effectiveness of the decomposition product as a catalyst is enhanced when the $NH_4OH$/Ni ratio in the preparation of the precursor compound is from about 1:1 to about 4:1, preferably about 1.5:1 to about 4:1, and more preferably about 2:1 to about 4:1. While not wishing to be bound by any particular theory or mechanism, there is some evidence the $NH_4OH$/Ni ratio causes the Ni—M—W—O phase to change in the decomposition product.

EXAMPLE 9

The catalysts of examples 1 and 2 were compared against standard supported Ni—Mo catalysts for the conversion of a LSADO (low sulfur auto diesel oil feed). This feed contained 510 wppm sulfur, 50 wppm nitrogen, and 30.6% aromatics with a gravity of 39.80 API. The catalysts were tested at 579° F., 650 psig of $H_2$, and 1850 SCFB/B of $H_2$. The relative activities of the different catalysts are summarized in Table 5.

TABLE 5

Relative Hydrotreating Activities on LSADO Feed

| Catalyst | Relative Volumetric HDS Activity | Relative Volumetric HDN Activity |
|---|---|---|
| $Ni,Mo/Al_2O_3$ | 1 | 1 |
| $NH_4$—NiMo—O | 0.25 | 0.50 |
| $NH_4$—$Ni_{1.0}Mo_{.5}W_{.5}$—O | 1.4 | 2.05 |

The Ni, $Mo/Al_2O_3$ catalyst is a standard HDN/HDS catalyst, the $NH_4$—Ni—Mo phase is the bulk phase with no tungsten, and the $NH_4$—$Ni_{1.0}Mo_{0.5}W_{0.5}$—O is the bulk phase with partial substitution of W for Mo. The $NH_4$—NiMo—O catalyst is also representative of known compounds. The catalyst of this invention is illustrated by $NH_4$—$Ni_{1.0}Mo_{0.5}W_{0.5}$—O and the data show the clear advantage of ammonium nickel tungsten molybdate for HDN activity.

EXAMPLE 10

Preparation of a bulk catalyst composition according to the solid route: 18.1 kg-ammonium dimolybdate (15.33 kg $MoO_3$) are dissolved in 575 liters water. Subsequently 28.5 kg ammonium metatungstate (24 69 kg $WO_3$) is added to the solution. The resulting solution is preheated up to 90° C. 26.5 kg $NiCO_3$ (49.7% Ni) powder is mixed with water and the resulting paste is added to the ammonium dimolybdate/ammonium metatungstate solution. The resulting mixture is reacted for 7 hours at 89° C.

EXAMPLE 11

Preparation of a bulk catalyst composition according to the solution route: In a 1-liter flask, 13.2 g ammonium molybdate.(0.075 moles Mo), 18.7 g ammonium metatungstate (0.075 moles W) and 43.6 g nickel nitrate hexahydrate (0.15 moles Ni) were dissolved in 300 ml water so that the resulting pH equaled 4.3. To this solution, a concentrated NH$_4$OH solution (about 600 ml) was added until the pH reached 10. At this point, some precipitate remained. The solution was refluxed at 100° C. for 3 hours. During this heating, the precipitate dissolved to give a clear blue solution and on further heating, a green precipitate formed. The heating was continued until the pH reached a value between 6.8 and 7.0. The suspension was cooled to room temperature, filtered, washed with water and dried at 120° C. overnight. 18 grams of material were obtained.

EXAMPLE 12
(Sample 2110587)

657 g of a NiMo—W bulk catalyst composition obtained according to the procedure described in Example 10 was added to 1362 g of an aqueous slurry containing 125 g of alumina (prepared by precipitation of sodium aluminate and aluminum sulfate). The resulting Ni—Mo—W bulk catalyst—alumina composition was subsequently mixed at 80° C. until an LOI of 31% was obtained. The resulting composition was subsequently extruded and the extrudates were dried at 120.C for about 90 minutes and subsequently calcined at 385° C. for one hour in air.

EXAMPLE 13
(Sample 2110598)

The process of Example 10 was repeated except that instead of the alumina suspension, a silica sol containing 10 wt. % silica were applied.

EXAMPLE 14
(Sample 2110591)

657 g of a Ni—Mo—W bulk catalyst composition obtained according to the procedure described in Example 10 was added to 510 g of a boehmite paste containing 125 g boehmite. The rebuffing paste was mixed at 60° C. to obtain an LOI of 42%. The resulting composition was extruded, dried and calcined as described in Example 12.

EXAMPLE 15
(Sample 2110469)

The procedure described in Example 10 was repeated except that alumina is present during the preparation of the bulk catalyst composition. To 755 g of the resulting dried Ni—Mo—W bulk catalyst—alumina composition containing 60 g alumina, 461 g water and a small amount of nitric acid were added. The resulting mixture was mixed at 70° C. while evaporating water until an LOI of 34% was obtained. The resulting composition was extruded, dried and calcined as described in Example 12.

EXAMPLE 16

Ammonium molybdate, ammonium tungsten and/or ammonium chromate are dissolved and combined in a first reactor. The temperature is increased to 90° C. The Group VIII salt is dissolved in a second reactor and heated to 90° C. Ammonium hydroxide is added to the first reactor to form a basic solution. The Group VIII metal solution is added to the first dropwise with stirring in 20 minutes. After 30 minutes, the precipitate is filtered and washed. The precipitate is dried overnight at 120° C. and calcined at 385° C.

EXAMPLE 17

The precipitation method of Example 16 was used to prepare a precipitate from ammonium dimolybdate, ammonium meta tungstate and Fe(III)(NO$_3$)$_3$·9 H$_2$O in 98% yield comprising 41.2 wt. % Fe$_2$O$_3$, 21.3 wt. % MoO$_3$, and 36.9 wt. % WO$_3$. The surface area of the precipitate was 76 m$^2$/g. The pore volume as measured up to 60 nm by BET using the adsorption curve was 0.147 ml/g.

EXAMPLE 18

The precipitation method of Example 16 was used to prepare a precipitate from Ni(CO$_3$)$_2$·6H$_2$O, (NH$_4$)$_6$Mo$_7$O$_{24}$·4H$_2$O, and (NH$_4$)$_2$Cr$_2$O$_7$ in 87.7% yield comprising 52.2 wt. % NiO, 29.4 wt. % MoO$_3$, and 16.6 wt. % Cr$_2$O$_3$. The surface area of the precipitate was 199 m$^2$/g. The pore volume as measured up to 60 nm by BET using the adsorption curve was 0.276 ml/g.

EXAMPLE 19

The precipitation method of Example 16 was used to prepare a precipitate from Ni(CO$_3$)$_2$·6H$_2$O, (NH$_4$)$_6$H$_2$W$_{12}$O$_{40}$, and (NH$_4$)$_2$Cr$_2$O$_7$ in 87.7% yield comprising 44.0 wt. % NiO, 42.4 wt. % WO$_3$, and 11.8 wt. % Cr$_2$O$_3$. The surface area of the precipitate was 199 m$^2$/g. The pore volume as measured up to 60 nm by BET using the adsorption curve was 0.245 ml/g.

Examples for Slurry Hydroprocessing

EXAMPLE 20 and 21 illustrate the preparation of the Mo-based high surface area conventional bulk catalyst and a bulk multimetallic catalyst (Mo—W—Ni-Based, hereinafter BMCat) of the present invention respectively. Example 22 provides activity comparison of the two catalyst systems for hydroprocessing of Arab Light vacuum resid. As shown in Table 6, the BMCat slurry catalyst of the present invention significantly improves HDS activity along with higher HDN and HDNi activity.

EXAMPLE 20

Mo-Based High Surface Area Conventional Catalyst

A solution of 22.6 g of phosphomolybdic acid (PMA from Fisher) in 140 g of deionized H$_2$O was mechanically blended in 600 g. of Arab Light Atmospheric resid (ALAR). After removing H$_2$O at 250° F.(121.1° C.), 572.6 g of resultant PMA-in-Oil concentrate were obtained having CCR to Mo atomic ratio and 50. liquid contents containing the dispersed catalyst was discharged. The liquid was separated from the catalyst and sent for analysis (Table 6.)

Table 6 presents activity comparison of the BMCat slurry catalyst of the present invention and the Mo-based high surface area conventional slurry catalyst. The BMCat slurry catalyst of the present invention demonstrates very high HDS acitivity, about 40% more active than Mo-based high surface area conventional slurry catalyst under the same conditions. In addition, nitrogen and Ni removal are also improved. An integration of the two catalyst systems projects a synergistic effect for improved overall contaminant removal from heavy feeds (Table 6).

Interestingly, the BMCat slurry catalyst of the present invention only displays modest CCR conversion compared to the Mo-based conventional slurry catalyst. It is suggested that the Mo, associated with hydrocarbonaceous materials, may provide high CCR selectivity. We intend to increase Mo concentration in the formulation of the BMCat slurry catalyst to enhance HDCCR activity.

TABLE 6

Activity Comparison of the BMCat Slurry Catalyst and the MO-based Conventional Slurry Catalyst

|  | BMCat Example 2 | Conventional Example 1 |
| --- | --- | --- |
| ALVR Charged, g | 100.1 | 100.3 |
| Cat Charged, g | 9.8 | 9.6 |
| Mo mol wt %, wt % on Feed | 0.0128, 1.23 | 0.0256, 2.46 |
| W mol wt %, wt % on Feed | 0.0128, 2.35 | 0, 0 |
| Ni mol wt %, wt % on Feed | 0.0256, 1.50 | 0, 0 |
| Slurry Performance |  |  |
| HDS, wt % | 55.3 | 40.7 |
| HDN, % | 40.1 | 31.3 |
| Ni removal, % | 98.4 | 80.1 |
| V removal, % | 99.8 | 96.5 |
| Concarbon Removal (CCR), wt % | 33.0 | 38.1 |

TABLE 7

Activity Comparison of Sulfided Ni/Mo/W Bulk Catalyst and Mo Based High Surface Area Conventional Bulk Catalyst
MSHP Conditions: 1000 psig; 775° F. (412.8° C.), 2 h
Sulfiding Conditions: 100 psig $H_2S$, 150° C., 30 min.

|  | Ni—Mo—W Catalyst | Conv. Bulk Catalyst |
| --- | --- | --- |
| ALVR Charged, g | 70 | 100 |
| Cat Charged, g | 6.0 | 4.8 |
| Mo, wt. % on Feed | 1.2 | 1.2 |
| W, wt. % on Feed | 2.4 | 0.0 |
| Ni, wt. % on feed | 1.97 | 0.0 |
| Slurry Performance |  |  |
| % HDS | 59 | 45 |
| % HDN | 24 | 30 |
| % HDM | 81 | 83 |
| % MCR removal | 32 | 33 |

EXAMPLE 23

Preparation of $NH_4$—$Ni_{1.5}$—$Mo_{0.5}$—$W_{0.5}$—O by direct precipitation

In a 1-liter flask, 17.65 g of ammonium molybdate (0.1 mole Mo) and 24.60 g of ammonium metatungstate (0.1 mole W) were dissolved in 700 ml of water giving a solution pH of ~5.2. To this solution 0.6 moles of $HN_4OH$ (45 ml of a 28–30% solution) was added, raising the solution pH to ~9.7 (solution A). This solution was warmed to 90° C. A second solution was prepared by dissolving 87.24 g of nickel nitrate hexahydrate, (0.3 moles Ni) in 50 ml of water (solution B). Solution B was heated to 90° C. and added dropwise at a rate of 5 ml/min into the ammonium molybdate/ammonium metatungstate solution. This suspension, which was at a pH ~4.5, was stirred for 30 min while the temperature was maintained at 90° C. The solid material was filtered hot and dried at 120° C. Approximately 61 g of material was recovered after drying. A total of 52.50 g (87% yield) was recovered after calcination in air at 400° C. This catalyst is designated bulk multimetallic catalyst (BMCat).

EXAMPLE 24

Hydrotreating Using BMCat

An autoclave was charged with 70 g of ALVR, and 2.0 g for BMCat precursor from Example 23. The reactor was heated to 150° C., after which the autoclave was charged with 100 psig $H_2S$ with stirring, and held at that temperature for 30 min. The autoclave was flushed out with hydrogen and heated to 320° C. under 1000 psig of static hydrogen. Hydrogen flow was started at 0.32 L/min as the autoclave was heated to 410° C. The mixture was stirred at these conditions for 2 hours. After cooling to about 150° C., the reactor was vented, and the contents filtered. The filtrate was analyzed for Ni, V, sulfur and nitrogen. Results using BMCat are shown in Table 7, and are compared to a comparable experiment where a Microcat was used. It should be noted that hydrogen flowed through the autoclave during the tests at rates corresponding to 0.32 or 0.45 L/min depending on the amount of feed used.

The Ni—Mo—W catalyst (BMCat) demonstrated higher HDS activity than Mo based higher surface area conventional bulk catalyst while still maintaining good HDM and MCR removal activity. An integration of this catalyst with other slurry type Mo based catalysts should improve overall contamination removal from heavy feeds.

What is claimed is:

1. A slurry hydroprocessinig process which comprises hydroprocessing a hydrocarbon feedstock selected from the group comprising distillate and residual feedstocks containing nitrogen and sulfur, under effective slurry hydrotreating conditions, in the presence of a hydrogen containing treat gas and of a bulk multimetallic catalyst for upgrading said hydrocarbon feedstock, wherein said bulk multimetallic catalyst comprises of at least one Group VIII non-noble metal and at least two Group VIB metals and wherein the ratio of said at least two Group VIB metals to said at least one Group VIII non-noble metal is from about 10:1 to about 1:10.

2. The process of claim 1, wherein said bulk multimetallic catalyst is represented by the formula:

$$(X)_b(Mo)_c(W)_dO_z$$

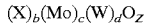

wherein X is a Group VIII non-noble metal, and the molar ratio of b: (c+d) is 0.5/1 to 3/1.

3. The process of claim 1, wherein said at least one Group VIII non-noble metal is selected from Ni and Co.

4. The process of claim 2, wherein said at least one Group VIII metal is Ni, and said bulk multimetallic catalyst has an X-ray diffraction pattern essentially amorphous with crystalline peaks at d=2.53 Angstroms and d=1.70 Angstroms.

5. The process of claim 1, wherein said bulk multimetallic catalyst is represented by the formula:

$$(X)_b(Mo)_c(W)_dO_z$$

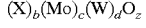

wherein X is a Group VIII non-noble metal, and the molar ratio of b: (c+d) is 0.75/1 to 1.5/1 and the molar ratio of c:d is 1/10 to 10/1.

6. The process of claim 1 wherein said hydrocarbon feedstock is a distillate selected from the group consisting of a product of a petroleum, synfuel, coal, shale oil, bitumen, or a tar sand conversion process.

7. The process of claim 1, wherein said hydrocarbon feedstock is a distillate boiling range feedstock boiling in the range of about 175° to about 400° C.

8. The process of claim 1, wherein said slurry hydrotreating conditions include a temperature in the range of about 290 to 370° C., pressures from about 300 to 1200 psig, and hydrogen treat rates of about 200 to 2000 standard cubic feet per hour.

* * * * *

UNITED STATES PATENT AND TRADEMARK OFFICE
CERTIFICATE OF CORRECTION

| | |
|---|---|
| PATENT NO. | : 6,712,955 B1 |
| APPLICATION NO. | : 09/869983 |
| DATED | : March 30, 2004 |
| INVENTOR(S) | : Zhiguo Hou et al. |

It is certified that error appears in the above-identified patent and that said Letters Patent is hereby corrected as shown below:

1) In col. 3, line 59: after "450°.," insert

-- hydrogen pressures of from 5 to 300 bar, liquid hourly space velocities of from 0.05 to 10 $h^{-1}$ and hydrogen treat gas rates of from 35.6 to 1780 $m^3/m^3$ (200 to 10000 SCF/B). The term "hydroprocessing" encompasses all processes in which a hydrocarbon feed is reacted with hydrogen at the temperatures and pressures noted above, and include hydrogenation, hydrotreating, hydrodesulfurization, hydrodenitrogenation, hydrodemetallation, hydrodearomatization, hydroisomerization, hydrodewaxing, and hydrocracking including selective hydrocracking. Depending on the type of hydroprocessing and the reaction conditions, the products of hydroprocessing may show improved viscosities, viscosity indices, saturates content, low temperature properties, volatilities and depolarization. It is to be understood that hydroprocessing of the present invention can be practiced in one or more reaction zones and can be practiced in either countercurrent flow or cocurrent flow mode. By countercurrent flow mode we mean a process mode wherein the feedstream flows countercurrent to the flow of hydrogen-containing treat gas. The hydroprocessing reactor can also be operated in any suitable catalyst-bed arrangement mode. For example, it can be a fixed bed, slurry bed, or ebulating bed.

A wide range of petroleum and chemical hydrocarbon feedstocks can be hydroprocessed in accordance with the present invention. Suitable feedstocks, which will typically contain both nitrogen and sulfur, include whole and reduced petroleum crudes, atmospheric and vacuum residua, asphaltenes, deasphalted oils, cycle oils, FCC tower bottoms, gas oils, including atmospheric and vacuum gas oils and coker gas oils, light to heavy distillates including raw virgin distillates,hydrocrackates, hydrotreated oils, dewaxed oils, slack waxes, Fischer-Tropsch waxes, raffinates, naphthas, and mixtures thereof.

Hydroprocessing of the present invention also includes slurry and ebullating bed hydroprocessing processes for the removal of sulfur and nitrogen compounds and the hydrogenation of aromatic molecules present in light fossil fuels such as petroleum mid-distillates. Hydroprocessing processes utilizing a slurry of dispersed catalysts in admixture with a hydrocarbon oil are generally known. For example, U.S. Pat. No. 4,557,821 to Lopez et al discloses hydrotreating a heavy oil employing a circulating slurry catalyst. Other patents disclosing slurry hydrotreating include U.S. Pat. Nos. 3,297,563; 2,912,375; and 2,700,015.

UNITED STATES PATENT AND TRADEMARK OFFICE
CERTIFICATE OF CORRECTION

PATENT NO. : 6,712,955 B1
APPLICATION NO. : 09/869983
DATED : March 30, 2004
INVENTOR(S) : Zhiguo Hou et al.

It is certified that error appears in the above-identified patent and that said Letters Patent is hereby corrected as shown below:

U.S. Patent Nos. 4,313,818 and 4,244,839 teach a method for preparing and using high surface area bulk metal catalysts by preparing them insitu the hydrocarbon oil feedstock. The metal precursor component is comprised of a thermally decomposable compound which is heated in the oil and in the presence of a hydrogen containing gas to produce a solid high surface area bulk metal catalyst. Both of these patents are incorporated herein by reference.

The slurry hydroprocessing process of the present invention can be practiced by introducing a distillate boiling range feedstock into a slurry hydroprocessing reactor. Before being passed to the hydroprocessing reactor, the feed is mixed with a hydrogen containing gas stream and heated to a reaction temperature in a furnace or preheater. Alternatively, the hydrogen gas can be introduced directly into the hydroprocessing reactor. The reactor contains the slurried catalyst as previously described. Recycle of the reactor effluent via a pump is optional to provide mixing within the reactor zone.

The process conditions in the hydroprocessing reactor will depend on such things as the particular feed being treated. In general, for distillate feeds, the slurry hydrotreating conditions will suitably be at a temperature of about 290 to 370°C, preferably about 315 to 345°C, and at a pressure of about 300 to 1200 psig, preferably about 500 to 800 psig. The hydrogen treat gas rate is suitably about 200 to 2000 SCF/B (standard cubic feet per barrel), preferably about 500 to 1500 SCF/B. The space velocity or holding time is suitably from about 0.5 to 4 hours and preferably about 1 to 2 hours.

The effluent from the distillate hydroprocessing reactor can be passed through a cooler and introduced into a gas-liquid separator or disengaging means where the hydrogen gas, along with ammonia and hydrogen sulfide by-products from the hydroprocessing reactions, may be separated from the liquid effluent and recycled back for reuse in the hydrogen stream. The recycled gas is usually passed through a scrubber to remove hydrogen sulfide and ammonia. This is usually recommended because of the inhibiting effect of such gases on the kinetics of hydrotreating and also to reduce corrosion in the recycle circuit. Fresh make-up hydrogen can be introduced into the recycle circuit. The liquid effluent from the gas-liquid separator can enter a solids separator, which may be a filter, vacuum flash, centrifuge or the like, in order to divide the hydrotreating reactor effluent into a catalyst stream and a product stream. The product in stream will be suitable for blending in the diesel pool and contains less than 5 ppm nitrogen and less than 20 wt. % aromatics. The product is typically reduced in sulfur as well.

UNITED STATES PATENT AND TRADEMARK OFFICE
CERTIFICATE OF CORRECTION

PATENT NO. : 6,712,955 B1
APPLICATION NO. : 09/869983
DATED : March 30, 2004
INVENTOR(S) : Zhiguo Hou et al.

It is certified that error appears in the above-identified patent and that said Letters Patent is hereby corrected as shown below:

In many cases, the product is given a light caustic wash to assure complete removal of $H_2S$. Small quantities of $H_2S$, if left in the product, will tend to oxidize to free sulfur upon exposure to the air, and may cause the product to exceed pollution or corrosion specifications.

Slurry hydroprocessing operations employing a circulating slurry catalyst are known to those familiar with petroleum processing. In a typical slurry hydroprocessing operation the slurry catalyst consisting of very small particles made up of extremely small crystallites exists as a substantially homogeneous dispersion in an oil or water/oil mixture. A typical slurry catalyst comprises Group VIB metal disulfide which is probably structured molecularly as basal platelets of Group VIB metal atoms separated by two layers of sulfur atoms with activity sites concentrated at the edge of each basal plane of the Group VIB metal atoms.

In most slurry hydroprocessing operations it is desirable to separate substantially all of the catalyst from the liquid hydrocarbon product. Thus, the separation step is typically carried out under conditions which maximize separation to produce a recyclable active catalyst product having a maximum concentration which can be pumped or conveyed to the feed. This is typically in the range of from about 5 weight percent ("wt. %") to about 75 wt. %, preferably in the range of from about 10 wt. % to about 50 wt. %, and even more preferably in the range of from about 15 wt. % to about 35 wt. %. The separation step may comprise the use of centrigues, cyclones, filters or even settling and draw-off.

The bulk multimetallic catalysts of the present invention can be prepared by several different methods. One preferred method for slurry hydroprocessing is to add one or more thermally decomposable metal compounds to the hydrocarbon feedstock, or to a side stream of the hydrocarbon feedstock. The thermally decomposable compound(s) will be representative of the one or more Group VIII non-noble metals and two or more Group VIB metals that comprise the bulk catalysts of this invention. A sufficient amount of the decomposable metal compound(s) are used to provide a ratio of atoms of Conradson carbon (calculated as elemental carbon) of feedstock to atoms of metal constituent of the thermally decomposable compound or compounds of less than about 750 to 1,preferably less than about 600 to 1, more preferably less than about 100 to 1. Suitable ranges of ratio of atoms of Conradson carbon of the feedstock to atom of metal constituent of the thermally decomposable metal compound or compounds include an atomic ratio ranging from about 2 to 1 to about 600 to 1, preferably from about 2 to 1 to about 300 to 1, more preferably from about 4 to 1 to about 100 to 1.

UNITED STATES PATENT AND TRADEMARK OFFICE
CERTIFICATE OF CORRECTION

| | |
|---|---|
| PATENT NO. | : 6,712,955 B1 |
| APPLICATION NO. | : 09/869983 |
| DATED | : March 30, 2004 |
| INVENTOR(S) | : Zhiguo Hou et al. |

It is certified that error appears in the above-identified patent and that said Letters Patent is hereby corrected as shown below:

Thus, the amount of thermally decomposable metal compound added will vary depending on the Conradson carbon of the oil feed actually used so as to provide the ratio required to obtain high surface area catalytic solids.

When the thermally decomposable metal compound or compounds are added to the feedstock oil, it first dissolves or disperses in the oil and subsequently, under catalytic preparation conditions herein described, is convered to the solid bulk multimetallic catalyst of the present invention.

The feedstock comprising the thermally decomposable metal compound or compounds is heated at a temperature ranging from about 200°C to about 570°C, preferably at a temperature ranging from about 260° to about 480°C, more preferably from about 315°C to about 450°C, at a pressure of either atmospheric or superatmospheric, preferably at superatmospheric in the presence of a hydrogen-containing gas, preferably one that also contains hydrogen sulfide. Suitable total pressures in the catalyst preparation zone when the heating step is being conducted include a pressure ranging up to about 5,000 psig, preferably ranging from about 100 to 3000 psig. Suitable reaction times include from about 5 minutes to about 4 hours, preferably from about 10 minutes to about 2 hours. Contact of the solution under catalyst preparation conditions in the reaction zone with the hydrogen containing gas converts the metal compound to the corresponding metal catalyst.

The oil containing the solids is removed from the catalyst preparation zone. The solids may be separated from the oil by conventional means, for example , by settling or centrifuging or filtration of the slurry. The recovered solids are the high surface area bulk catalysts of this invention.

The feedstream is contacted at hydroprocessing conditions with a bulk catalyst containing at least one Group VIB metal and at least one Group VIII metal, preferably two Group VIB metals and one Group VIII metals, more preferably Ni-Mo-W. The bulk catalyst compositions of the present invention can be prepared by an ex-situ process wherein all of the metal precursor components are in solution in a protic liquid or where not all of the metal components are in solution. That is, a process which comprises contacting at least one Group VIII non-noble metal component with at least one Group VIB metal component in the presence of a protic liquid wherein during contacting not all of the Group VIB and/or Group VIII non-noble metals are in solution.

UNITED STATES PATENT AND TRADEMARK OFFICE
CERTIFICATE OF CORRECTION

PATENT NO. : 6,712,955 B1
APPLICATION NO. : 09/869983
DATED : March 30, 2004
INVENTOR(S) : Zhiguo Hou et al.

It is certified that error appears in the above-identified patent and that said Letters Patent is hereby corrected as shown below:

Another method for preparing the catalysts of the presnt invention is where not all of the metals are in solution. Generally, the contacting of the metal components in the presence of the protic liquid comprises mixing the metal component and subsequently reacting the resulting mixture. It is essential to the solid route that at least one metal components is added at least partly in the solid state during the mixing step and that the metal of at least one of the metal components which have been added at least partly in the solid state, remains at least partly in the solid state during the mixing and reaction step. "Metal" in this context does not mean the metal in its metallic form but present in a metal compound, such as the metal component as initially applied or as present in the bulk catalyst composition.

Generally, during the mixing step for the ex-situ preparation method, either at least one metal component is added at least partly in the solid state and at least one metal component is added in the solute state, or all metal components are added at least partly in the solid state, wherein at least one of the metals of the metal components which are added at least partly in the solid state remains at least partly in the solid state during the entire process of the solid route. That a metal component is added "in the solute state" means that the whole amount of this metal component is added as a solution of this metal component in the protic liquid. That a metal component is added "at least partly in the solid state" means that at least part of the metal component is added as solid metal component and, optionally, another part of the metal component is added as a solution of this metal component in the protic liquid. A typical example is a suspension of a --

2) in col. 20, line 47: after "and 50." insert

-- Next, 200 g of the PMA-In-Oil concentrate were charged to a 300 cc stirred autoclave and pressurized to 100 psig $H_2S$. The mixture was heated to 300°F(148.9°C) for 40 minutes under 100 psig $H_2S$, and then heated to 725°F(385°C) for 30 minutes after removing unreacted $H_2S$, and then cooled rapidly. The autoclave was vented and flushed with N2, and the slurry mixture was discharged. The solids were isolated by filtration, washed with toluene and dried under vacuum. Solids yield: 7.04 g of high surface area catalyst.

UNITED STATES PATENT AND TRADEMARK OFFICE
CERTIFICATE OF CORRECTION

PATENT NO. : 6,712,955 B1
APPLICATION NO. : 09/869983
DATED : March 30, 2004
INVENTOR(S) : Zhiguo Hou et al.

It is certified that error appears in the above-identified patent and that said Letters Patent is hereby corrected as shown below:

Example 21 BMCat SlurryCatalyst (MoJWINi = 1:1:2):
A solution of 11.3 g of phosphomolybdic acid (PMA from Fisher), 13.7 g of phosphotungstic acid (PTA from Fisher) and 28.5 g of nickel acetate (Fisher) in 140 g of deionized $H_2O$ was mechanically blended in 600 g of ALAR. After removing $H_2O$ at 250°F(121.1°C), 540.8 g of catalyst concentrate were obtained having CCR to Mo + W atomic ratio about 50.

The dry precursor concentrate was then converted to catalyst concentrate using the procedure described in Example 20. The yield of catalyst solid obtained from 100 g of the precursor was 7.21g.

Example 22 Activity comparison of the catalysts:

The catalysts of Examples 20 and 21 were compared in a standard autoclave test wherein 100 g of Arab Light vacuum resid (ALVR) were treated under mild conditions, 750°F(398.9°C) and 1000 psig of hydrogen pressure. Hydrogen was flowed through the autoclave during the test at rate corresponding to 0.45 L/min. The autoclave was heated to 750°F over a period of 20 minutes, held at this temperature for 2 hours, and cooled rapidly. The autoclave was vented and the --

Signed and Sealed this

Ninth Day of January, 2007

JON W. DUDAS
*Director of the United States Patent and Trademark Office*